United States Patent
Miga et al.

(10) Patent No.: US 7,072,705 B2
(45) Date of Patent: Jul. 4, 2006

(54) APPARATUS AND METHODS OF BRAIN SHIFT COMPENSATION AND APPLICATIONS OF THE SAME

(75) Inventors: Michael I. Miga, Franklin, TN (US); Prashanth Dumpuri, Nashville, TN (US); Chun-Cheng R. Chen, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 28 days.

(21) Appl. No.: 10/988,982

(22) Filed: Nov. 15, 2004

(65) Prior Publication Data
US 2005/0101855 A1 May 12, 2005

Related U.S. Application Data

(63) Continuation-in-part of application No. 10/936,339, filed on Sep. 8, 2004.

(60) Provisional application No. 60/501,514, filed on Sep. 8, 2003.

(51) Int. Cl.
*A61B 5/055* (2006.01)
(52) U.S. Cl. ........................ 600/411; 600/427
(58) Field of Classification Search ................ 600/410, 600/425, 437, 411, 427; 382/128–131, 168–170; 324/309, 318
See application file for complete search history.

(56) References Cited

U.S. PATENT DOCUMENTS

| 6,006,126 | A * | 12/1999 | Cosman ........................ 600/426 |
| 6,272,370 | B1 * | 8/2001 | Gillies et al. ................ 600/411 |
| 2003/0071194 | A1 * | 4/2003 | Mueller et al. ........... 250/208.1 |
| 2004/0013289 | A1 * | 1/2004 | Labudde ..................... 382/128 |
| 2004/0046557 | A1 * | 3/2004 | Karmarkar et al. ......... 324/322 |

OTHER PUBLICATIONS

C. R. Maurer, J. M. Fitzpatrick, M. Y. Wang, R. L. Galloway, R. J. Maciunas, and G. S. Allen, "Registration of head volume images using implantable fiducial markers," *IEEE Trans. Med. Imag.*, vol. 16, pp. 447-462, Apr. 1997.

(Continued)

*Primary Examiner*—Eleni Mantis-Mercader
(74) *Attorney, Agent, or Firm*—Morris Manning & Martin; Tim Tingkang Xia, Esq.

(57) ABSTRACT

A method of compensation for intra-operative brain shift of a living subject. In one embodiment, the method includes the steps of pro-operatively acquiring brain images of the living subject, constructing a statistical atlas of brain displacements of the living subject from the pro-operatively acquired brain images, intra-operatively measuring brain displacements of the living subject, deriving an intra-operative displacement atlas from the intra-operatively measured brain displacements and the statistical atlas, obtaining intra-operative brain shift at least from the intra-operative displacement atlas, and compensating for the intra-operative brain shift.

33 Claims, 6 Drawing Sheets

OTHER PUBLICATIONS

W. E. L. Grimson, G. J. Ettinger, S. J. White, T. Lozano Perez, W. M. Wells, and R. Kikinis, "An automatic registration method for frameless stereotaxy, image guided surgery, and enhanced reality visualization," *IEEE Trans. Med. Imag.*, vol. 15, pp. 129-140, Feb. 1996.

C. R. Maurer, R. J. Maciunas, and J. M. Fitzpatrick, "Registration of head CT images to physical space using a weighted combination of points and surfaces," *IEEE Trans. Med. Imag.*, vol. 17, pp. 753-761, May 1998.

M. A. Audette, K. Siddiqi, and T. M. Peters, "Level-set surface segmentation and fast cortical range image tracking for computing intra-surgical deformations," in *Lecture Notes in Computer Science*.New York: Springer-Verlag, 1999, vol. 1679, Medical Image Computing and Computer Assisted Intervention: MICCAI'99, pp. 788-797.

A. Raabe, R. Krishnan, R. Wolff, E. Hermann, M. Zimmermann, and V. Seifert, "Laser surface scanning for patient registration in intracranial image-guided surgery," *Neurosurgery*, vol. 50, No. 4, pp. 797-801, 2002.

M. A. Audette, F. P. Ferrie, and T. M. Peters, "An algorithmic overview of surface registration techniques for medical imaging," *Med. Image Anal.*, vol. 4, No. 3, pp. 201-217, 2000.

R. L. Galloway, "The process and development of image-guided procedures," *Annu. Rev. Biomed. Eng.*, vol. 3, pp. 83-108, 2001.

D. L. G. Hill, C. R. Maurer, R. J. Maciunas, J. A. Barwise, J. M. Fitzpatrick, and M. Y. Wang, "Measurement of intra-operative brain surface deformation under a craniotomy," *Neurosurgery*, vol. 43, No. 3, pp. 514-526, 1998.

D. W. Roberts, A. Hartov, F. E. Kennedy, M. I. Miga, and K. D. Paulsen, "Intra-operative brain shift and deformation: A quantitative analysis of cortical displacement in 28 cases," *Neurosurgery*, vol. 43, No. 4, pp. 749-758, 1998.

C. Nimsky, O. Ganslandt, S. Cerny, P. Hastreiter, G. Greiner, and R. Fahlbusch, "Quantification of, visualization of, and compensation for brain shift using intra-operative magnetic resonance imaging," *Neurosurgery*, vol. 47, No. 5, pp. 1070-1079, 2000.

A. Nabavi, P. M. Black, D. T. Gering, C. F. Westin, V. Mehta, R. S. Pergolizzi, M. Ferrant, S. K. Warfield, N. Hata, R. B. Schwartz, W. M. Wells, R. Kikinis, and F. A. Jolesz, "Serial intra-operative magnetic resonance imaging of brain shift," *Neurosurgery*, vol. 48, No. 4, pp. 787-797, 2001.

C. Nimsky, O. Ganslandt, H. Kober, M. Buchfelder, and R. Fahlbusch, "Intra-operative magnetic resonance imaging combined with neuronavigation: A new concept," *Neurosurgery*, vol. 48, No. 5, pp. 1082-1091, 2001.

W. E. L. Grimson, R. Kikinis, F. A. Jolesz, and P. M. Black, "Imageguided surgery," *Sci. Amer.*, vol. 280, No. 6, pp. 62-69, 1999.

C. Nimsky, O. Ganslandt, P. Hastreiter, and R. Fahlbusch, "Intra-operative compensation for brain shift," *Surg. Neurol.*, vol. 56, No. 6, pp. 357-364, 2001.

M. Knauth, N. Aras, C. R. Wirtz, A. Dorfler, T. Engelhorn, and K. Sartor, "Surgically induced intracranial contrast enhancement: Potential source of diagnostic error in intra-operative mr imaging," *Amer. J. Neuroradiol.*, vol. 20, No. 8, pp. 1547-1553, 1999.

G. R. Sutherland, T. Kaibara, C. Wallace, B. Tomanek, and M. Richter, "Intra-operative assessment of aneurysm clipping using magnetic resonance angiography and diffusion-weighted imaging: Technical case report," *Neurosurgery*, vol. 50, No. 4, pp. 893-897, 2002.

D. G. Gobbi, R. M. Comeau, and T. M. Peters, "Ultrasound/mri overlay with image warping for neurosurgery," in *Lecture Notes in Computer Science*. New York: Springer-Verlag, 2000, vol. 1935, Medical Image Computing and Computer-Assisted Intervention: MICCAI'00, pp. 106-114. (Manuscript Provided).

D. W. Roberts, M. I. Miga, A. Hartov, S. Eisner, J. M. Lemery, F. E. Kennedy, and K. D. Paulsen, "Intra-operatively updated neuroimaging using brain modeling and sparse data," *Neurosurgery*, vol. 45, No. 5, pp. 1199-1206, 1999.

M. I. Miga, K. D. Paulsen, J. M. Lemery, S. D. Eisner, A. Hartov, F. E. Kennedy, and D. W. Roberts, "Modeling-updated image guidance: Initial clinical experiences with gravity-induced brain deformation," *IEEE Trans. Med. Imag.*, vol. 18, pp. 866-874, Oct. 1999.

M. I. Miga, K. D. Paulsen, F. E. Kennedy, P. J. Hoopes, A. Hartov, and D. W. Roberts, "In vivo analysis of heterogeneous brain deformation computations for model-updated image guidance," *Comput. Methods Biomech. Biomed. Eng.*, vol. 3, No. 2, pp. 129-146, 2000. (Manuscript Provided).

G. E. Christensen, R. D. Rabbitt, and M. I. Miller, "3D brain mapping using a deformable neuroanatomy," *Phys. Med. Biol.*, vol. 39, No. 3, pp. 609-618, 1994.

S. Nakajima, H. Atsumi, R. Kikinis, T. M. Moriarty, D. C. Metcalf, F. A. Jolesz, and P. M. Black, "Use of cortical surface vessel registration for image-guided neurosurgery," *Neurosurgery*, vol. 40, No. 6, pp. 1201-1208, 1997.

C. Studholme, D. L. G. Hill, and D. J. Hawkes, "An overlap invariant entropy measure of 3d medical image alignment," *Pattern Recognit.*, vol. 32, No. 1, pp. 71-86, 1999.

M. A. Biot, "General theory of three-dimensional consolidation," *Journal of Applied Physics*, vol. 12, pp. 155-164, 1941.

T. Nagashima, S. Takayuki, and S. I. Rapoport, "A two-dimensional, finite element analysis of vasogenic brain edema," *Neurol Med Chir (Tokyo)*, vol. 30, pp. 1-9, 1990.

K. D. Paulsen, M. I. Miga, F. E. Kennedy, P. J. Hoopes, A. Hartov, and D. W. Roberts, "A computational model for tracking subsurface tissue deformation during stereotactic neurosurgery," *IEEE Transactions on Biomedical Engineering*, vol. 46, pp. 213-225, 1999.

M. Ferrant, A. Nabavi, B. Macq, P. M. Black, F. A. Jolesz, R. Kikinis, and S. K. Warfield, "Serial registration of intra-operative MR images of the brain," *Medical Image Analysis*, vol. 6, pp. 337-359, 2002.

P. J. Besl, and N.D. Mc Kay, "A method of registration of 3-D shapes," *IEEE Tran. On Pattern Analysis and Machine Intelligence 14(2): 239-256.* (1992).

O. Skrinjar, D. Spencer, and J. Duncan, "Brain shift modeling for use in neurosurgery," in *Medical Image Computing and Computer-Assisted Intervention—Miccai'98*, vol. 1496, *Lecture Notes in Computer Science*, pp. 641-649, 1998. (Manuscript Provided).

C. Davatzikos, D. G. Shen, A. Mohamed, and S. K. Kyriacou, "A framework for predictive modeling of anatomical deformations," *IEEE Transactions on Medical Imaging*, vol. 20, pp. 836-843, 2001.

A. E., Johnson S. B. Kang Registration and integration of textured 3D data. *Image and Vision Computing* 17(2): 135-147, (1999).

T.K. Sinha, D. M. Cash, R. J. Weil, R. L. Galloway, M. I. Miga, "*Cortical Surface Registration Using Texture Mapped Point Clouds and Mutual Information*" Lecture Notes in Computer Science: Medical Image Computing and Computer-Assisted Intervention—MICCAI 2002, Springer-Verlag, New York, vol. 2488, Part 2, pp. 533-540, 2002 (Manuscript Provided).

T. K. Sinha, D. M. Cash, R. J. Weil, R. L. Galloway, M. I. Miga. "*Textured Laser Range Scanning and Registration of the Cortical Surface,*" *24th Annual International Conf. Of EMBS and BMES, 2002*. (Manuscript Provided).

M. I. Miga, T. K. Sinha, D. M. Cash, R. L. Galloway, and R. J. Weil, "Cortical Surface Registration for Image-Guided Neurosurgery Using Laser-Range Scanning," IEEE Transactions on Medical Imaging, vol. 22, No. 8, pp. 973-985, 2003. (Manuscript Provided).

V. Duay, T. K. Sinha, P. D'Haese, M. I. Miga, B. M. Dawant, "Non-Rigid Registration of Serial Intra-Operative Images For Automatic Brain-Shift Estimation," Lecture Notes in Computer Science: Second International Workshop on Biomedical Image Registration—WBIR 2003, vol. 2717, pp. 61-70, 2003. (Manuscript Provided).

T.K. Sinha, D. M. Cash, R. J. Weil, R. L. Galloway, M. I. Miga, "*Laser Range Scanning for Cortical Surface Characterization During Neurosurgery,*" *Medical Imaging 2003: Visulization, Image-guided Procedures, and Display: Proc. Of the SPIE*, vol. 5029, pp. 98-107 (Manuscript Provided).

H. J. Nauta, "Error assessment during "image guided" and "imaging interactive" stereotactic surgery", *Comput. Med. Imag. Graphics*, vol. 18, No. 4, pp. 279-287, 1994.

P. Dumpuri, R. C. Chen, M. I. Miga, "Model Updated Image Guidence: A Statistical Approach", Lecture Notes in Computer Science: Medical Image Computing and Computer-Assisted Intervention—MICAAI 2003, vol. 2879, Part 1, pp. 375-382, 2003.

Michel A. Audette, Kaleem Siddiqui, Frank P. Ferrie, and Terry M. Peters, "*An Integrated Range-Sensing, Segmentation And Registration Framework For The Characterization Of Intra-Surgical Brain Deformations In Image-Guided Surgery*", Computer Vision and Image Understanding, vol. 89, pp. 226-251, 2003.

* cited by examiner

1

APPARATUS AND METHODS OF BRAIN SHIFT COMPENSATION AND APPLICATIONS OF THE SAME

CROSS-REFERENCE TO RELATED PATENT APPLICATION

This application is a continuation-in-part of U.S. patent application Ser. No. 10/936,339, filed Sep. 8, 2004, entitled "APPARATUS AND METHODS OF CORTICAL SURFACE REGISTRATION AND DEFORMATION TRACKING FOR PATIENT-TO-IMAGE ALIGNMENT IN RELATION TO IMAGE-GUIDED SURGERY," by Michael I. Miga, Benoit M. Dawant and Tuhin K. Sinha, the disclosure of which is hereby incorporated herein by reference in its entirety, which itself claims the benefit, pursuant to 35 U.S.C. §119(e), of provisional U.S. patent application Ser. No. 60/501,514, filed Sep. 8, 2003, entitled "APPARATUS AND METHODS OF CORTICAL SURFACE REGISTRATION AND DEFORMATION TRACKING FOR PATIENT-TO-IMAGE ALIGNMENT DURING IMAGE-GUIDED SURGERY," by Michael I. Miga, Benoit M. Dawant and Tuhin K. Sinha, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [28] represents the 28th reference cited in the reference list, namely, M. I. Miga, K. D. Paulsen, J. M. Lemery, S. D. Eisner, A. Hartov, F. E. Kennedy, and D. W. Roberts, "Model-updated image guidance: Initial clinical experiences with gravity-induced brain deformation," *IEEE Trans. Med. Imag.*, vol. 18, pp. 866–874, October 1999.

FIELD OF THE INVENTION

The present invention generally relates to image-guided surgery, and in particular to apparatus and methods of compensation for brain shifts in relation to image-guided surgery.

BACKGROUND OF THE INVENTION

Image-guided surgery (hereinafter "IGS") involves patient-specific anatomical images pre-operatively acquired that spatially localize pathology, digitization technology that allows the identification and tracking of targeted points of interest in a patient's physical space in an operating room (hereinafter "OR"), and alignments of the patient-specific images to the patient's physical space in the OR such that the digitization technology can be referenced to the patient-specific images and used for guidance during surgery. Central to the IGS is the method of registering an image space (a coordinate system corresponding to the pre-operative images) to a physical space (a coordinate system corresponding to the intra-operative anatomy of the patient). Once the registration is performed, all pre-operative planning and acquired data related to the patient's anatomy could be displayed intra-operatively to a surgeon and used for assistance in surgical guidance and treatment.

Over to past years, a variety of registration methods have been developed. Among them, a point-based registration (hereinafter "PBR") has been mostly characterized and thoroughly examined, whereby landmarks are localized in patient's image volumes and aligned with corresponding landmarks digitized in physical space of the patient intra-operatively. The landmarks, or fiducials, can be either natural structures such as a nose bridge of the patient, or synthetic components such as small cylindrical markers adhered to the skin of the patient or markers implanted into the skull of the patient prior to image acquisitions [1,2]. Further analysis of configurations of fiducial markers, optimum marker numbers, and effects on target localization error has been reported [2]. The PBR technique has proven clinically accurate and useful. However, utilization of the PBR method requires a preliminary surgery for implantation of the fiducial markers to predetermined positions in a patient's anatomy.

Another technique for the registration is accomplished by identifying two geometric surfaces that are the same in an image space and a physical space of a patient, respectively, and aligning them between the two spaces. The ability to acquire surface data using a probe, such as optical probe, electromagnetic probe, and/or ultrasound probe, and lasers [3–7] in conjunction with surface extraction algorithms applied to imaging data has led to new methods of surface based registrations [8]. The primary difference between the surface-based registration and the PBR is that the surface based registration does not require a one-to-one point correspondence. On the other hand, an averaging effect in the surface-based registration serves to reduce uncorrelated localization error generated during the acquisition of spatially well-resolved surface data. However, the surface based alignment techniques are limited with facts, for example, scalps lack geometric specificity, and skin surfaces may deform due to intra-operative drugs or procedural retraction [9]. An alternative registration technique, less commonly used for IGS purposes, is an intensity-based or volume registration approach [2], which is usually applied for alignments of a source image volume to a target image volume.

However, recent studies have shown limitations in accuracy with current image-guided procedures. The discrepancy observed is a by-product of the rigid-body assumptions and techniques used during the registration process. Specifically, with neurosurgery, registration is provided by markers attached to the skull of a patient or on the skin surrounding the skull of a patient, where soft-tissue deformations of the brain during surgery may result in significant errors in aligning a pre-operative image space to an actual physical space. One of the earliest observed instances of the error was reported by Kelly et al. [10]. More recently, Nauta has measured this shift that is of an order of 5 mm [11]. Subsequent investigations in intra-operative brain surface movements have shown that an average deformation for brain shifts is about 1 cm. Moreover, predispositions for brain movement in the direction of gravity have been investigated [12, 13].

This has lead studies to develop methods and techniques that can compensate for intra-operative brain shifts. One of the methods includes the use of conventional imaging modalities during surgery, i.e. intra-operative computed tomography (hereinafter "iCT"), intra-operative magnetic resonance (hereinafter "iMR"), and/or intra-operative ultrasound (hereinafter "iUS") imaging. When available, intra-operative images are registered to pre-operative images using a number of nonrigid intra-modal and/or inter-modal registration methods. In the 1980s, there was a significant effort to incorporate iCT during surgery as a means for acquiring intra-operative image series. However, dose considerations of repeatedly using computed tomography (hereinafter "CT") scanning in the OR have hindered adoption of the iCT technique [14]. More recently, several medical centers have explored the use of iMR imaging for data acquisition and shift compensation [15–18] and have developed elegant and sophisticated methods for visualization in the OR [3, 19, 20]. Although conceptually appealing, the exorbitant cost and cumbersome nature of such a system (e.g., need for a MR compatible OR) have left their widespread adoption uncertain. In addition to these logistical concerns, recent reports have demonstrated potential problems related to surgically induced contrast enhancement that could be often confused with contrast-enhancing residual tumor [21], and image distortions from susceptibility and/or eddy current artifacts related to the presence of MR compatible Yasargil clips for aneurysm clipping procedures [22]. An alternative to iCT and iMR imaging is the use of iUS [23–26], where locally reconstructed iUS image volumes may provide a real-time guidance feedback. However, the quality of the iUS images over the course of surgery limits their effectiveness in shift compensation.

A possible alternative to high-cost intra-operative imaging is to use computational methods to compensate for brain shifts in IGS. A strategy for using computational methods to correct for brain shifts in neurosurgery was highlighted by Roberts et al. [27]. Rapidly acquiring minimally invasive data that describes changes in brain geometry during surgery is necessary to develop a computational approach that accounts for brain deformations. In these methods, intra-operative surface data are combined with a statistical and/or mathematical model of the soft-tissue mechanics that describe brain deformation [27]. Physical models have been successfully used to reconstitute 70% to 80% of the shift occurring under loads similar to a clinical setting. A detailed work regarding the fidelity of such computations within animal and human systems has been reported [28, 29]. Registrations of multimodality images by elastic matching technique have also been studied [30, 31]. Deformable templates for large deformation warping of images have been utilized [32]. However, the computational methods may not be able to effectively predict the extent of tumor margins. On the other hand, the next important question is how to integrate intra-operative measurements within a framework that is feasible for the OR use. A makeshift approximation is to apply all measurements as displacement boundary conditions within the model and move forward. This approach has been utilized by Ferrant et al. [49] within the context of iMR and treats the computational model as an interpolator. Although intuitive, this approach may not work for a model-based compensation platform in medical centers without an iMR system.

Therefore, a heretofore unaddressed need exists in the art to address the aforementioned deficiencies and inadequacies.

SUMMARY OF THE INVENTION

The present invention provides apparatus and methods of compensation for intra-operative brain shift of a living subject, being a human being or animal, which are cost-effective, clinically translatable, scalable to medical centers and facilities, and tractable.

In one aspect, the present invention relates to a method of compensation for intra-operative brain shift of a living subject. In one embodiment, the method includes the step of pro-operatively acquiring brain images of the living subject. The pro-operatively acquired brain images of the living subject comprise image data with respect to the brain surface geometry, where the image data with respect to the brain surface geometry is obtained through the use of at least one of positron emission tomography device, electroencephalography device, computer tomography device, functional magnetic resonance imaging device, magnetic resonance imaging device, and ultrasound imaging device.

The method further includes the step of constructing a statistical atlas, [E], of brain displacements of the living subject from the pro-operatively acquired brain images, where [E] is in the form of an n×m matrix with n, m being integers. In one embodiment, the step of constructing the statistical atlas [E] of brain displacements of the living subject has the steps of obtaining m model solutions corresponding to a pre-operative surgical plan for the living subject using a finite element mesh having n nodes, and generating the statistical atlas [E] in the form of an n×m matrix with each model solution E, which is in the form of a n×1 matrix, forming a column of the matrix. The pre-operative surgical plan, in one embodiment, provides a range of orientations of the head of the living subject with respect to the direction of gravity and amounts of cerebrospinal fluid drainage of the brain of the living subject. The model solutions are obtained by solving the equations of:

$$\nabla \cdot G \nabla U + \nabla \frac{G}{1-2v}(\nabla \cdot U) - \alpha \nabla p + (\rho_t - \rho_f)g = 0; \text{ and} \quad (i).$$

$$\alpha \frac{\partial}{\partial t}(\nabla \cdot U) + \frac{1}{S}\frac{\partial p}{\partial t} - \nabla \cdot k\nabla p = 0, \quad (ii).$$

where U is a displacement vector, G is a shear modulus, v is a Poisson's ratio, p is an interstitial fluid pressure, α is a ratio of fluid volume extracted to volume change of the tissue under compression, k is a hydraulic conductivity, 1/S is an amount of fluid forced into the tissue under constant volume, $\rho_t$ is the density of tissue, $\rho_f$ is the density of fluid, and g is the gravitational acceleration vector. The equations (i) and (ii) are solved further with boundary conditions corresponding to specific structures of the brain of the living subject. In one embodiment, the specific structures of the brain of the living subject include at least one of a falx cerebri, tentorium cerebelli, lateral ventricle, white matter, gray matter, tumor, and any combination thereof. In another embodiment, the specific structures of the brain of the living subject comprise at least one of edema-induced swelling, mannitoi-induced shrinking, and any combination thereof. In one embodiment, the statistical atlas [E] is in the form of $$[E] = \{E_{ij}\} = \begin{bmatrix} U_1^1 & U_1^2 & \cdots & \cdots & U_1^m \\ U_2^1 & U_2^2 & \cdots & \cdots & U_2^m \\ \cdots & \cdots & \cdots & \cdots & \cdots \\ \cdots & \cdots & \cdots & \cdots & \cdots \\ U_n^1 & U_n^2 & \cdots & \cdots & U_n^m \end{bmatrix},$$

where $E_{ij}=U_i^j$ is a brain displacement value for i-th nodal position on the finite element mesh at the j-th orientation and cerebrospinal fluid drainage level, and where $1 \leq i \leq n$, and $1 \leq j \leq m$.

Moreover, the method includes the step of intra-operatively measuring brain displacements, $\{f\}$, of the living subject, where $\{f\}$ is in the form of a n×1 matrix. The step of measuring intra-operative brain displacements, in one embodiment, is performed with an optical device that is capable of obtaining frequency, intensity and geometric data with respect to the cortical surface of the living subject simultaneously. The optical device is a laser range scanner. Other image acquiring devices may also be utilized to practice the present invention.

The method also includes the step of deriving an intra-operative displacement atlas, $[X_f]$, from the intra-operatively measured brain displacements $\{f\}$ and the statistical atlas $[E]$.

Additionally, the method includes the step of obtaining intra-operative brain shift at least from the intra-operative displacement atlas $[X_f]$. In one embodiment, the step of obtaining the intra-operative brain shift has the steps of minimizing the function $\|[E]\{x\}-\{f\}\|$ subject to $\{x\} \geq 0$, so as to obtain regression coefficients $\{x\}$, where the sum of the regression coefficients $\{x\}$ is subject to unity, and calculating the intra-operative brain shifts of the living subject from the following relation:

$$\{\text{Intra-operative brain shift}\}=[X_f]^*\{x\},$$

where $\{x\}$ are the regression coefficients obtained in the minimizing step. The minimizing step, in one embodiment, is performed with a least-squares regression algorithm.

Furthermore, the method includes the step of compensating for the intra-operative brain shift. The compensating step in one embodiment has the step of updating the pre-operatively acquired images of the living subject with the intra-operatively measured brain displacements.

In another aspect, the present invention relates to a system of compensation for intra-operative brain shift of a living subject. In one embodiment, the system has an imaging acquiring device for pro-operatively acquiring brain images of the living subject. The imaging acquiring device includes at least one of positron emission tomography device, electroencephalography device, computer tomography device, functional magnetic resonance imaging device, magnetic resonance imaging device, and ultrasound imaging device.

Furthermore, the system has a scanning device for intra-operatively measuring brain displacements of the living subject. The scanning device, in one embodiment, has a laser range scanner that is capable of obtaining frequency, intensity and geometric data with respect to the cortical surface of the living subject simultaneously. In another embodiment, the scanning device has an ultrasound device. Other types of scanning services may also be utilized to practice the present invention.

Moreover, the system has at least one computer that is coupled with the image acquiring device and the optical device and adapted for performing the steps of constructing a statistical atlas of brain displacements of the living subject from the pro-operatively acquired brain images, deriving an intra-operative displacement atlas from the intra-operatively measured brain displacements and the statistical atlas, obtaining intra-operative brain shift at least from the intra-operative displacement atlas, and compensating for the intra-operative brain shift.

In one embodiment, the step of constructing the statistical atlas of brain displacements of the living subject comprises the steps of obtaining m model solutions corresponding to a pre-operative surgical plan for the living subject using a finite element mesh having n nodes; and generating the statistical atlas in the form of an n×m matrix, $[E]$, with each model solution, E, which is in the form of a n×1 matrix, forming a column of the matrix.

The step of obtaining the intra-operative brain shift includes the steps of minimizing the function $\|[E]\{x\}-\{f\}\|$ subject to $\{x\} \geq 0$, so as to obtain regression coefficients $\{x\}$, where the sum of the regression coefficients $\{x\}$ is subject to unity, and calculating the intra-operative brain shifts of the living subject from the following relation:

$$\{\text{Intra-operative brain shift}\}=[X_f]^*\{x\},$$

where $\{x\}$ are the regression coefficients obtained in the minimizing step. The minimizing step is performed with a least-squares regression algorithm. In one embodiment, the compensating step includes the step of updating the pre-operatively acquired images of the living subject with the intra-operatively measured brain displacements.

Additionally, the system has a display device coupled to the at least one computer for displaying the brain shift dynamically to facilitate the diagnostic or surgical procedure.

In yet another aspect, the present invention relates to a method of compensation for intra-operative brain shift of a living subject. In one embodiment, the method includes the steps of constructing a statistical atlas from pre-operatively acquired brain images of the living subject, calculating brain displacements of the living subject for a given set of the living subject's orientation and amount of cerebrospinal fluid drainage from the statistical atlas, intra-operatively measuring brain displacements of the living subject, obtaining the intra-operative brain shift from the calculated brain displacements and the measured brain displacements, and compensating the intra-operative brain shift. The intra-operative brain shift, in one embodiment, may be corresponding to distributed loading conditions that are associated with gravity, edema-induced swelling, mannitoi-induced shrinking, and the likes. In another embodiment, the intra-operative brain shift may be corresponding to surface-based loading conditions that are associated with tissue retraction, tissue resection, and the likes.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
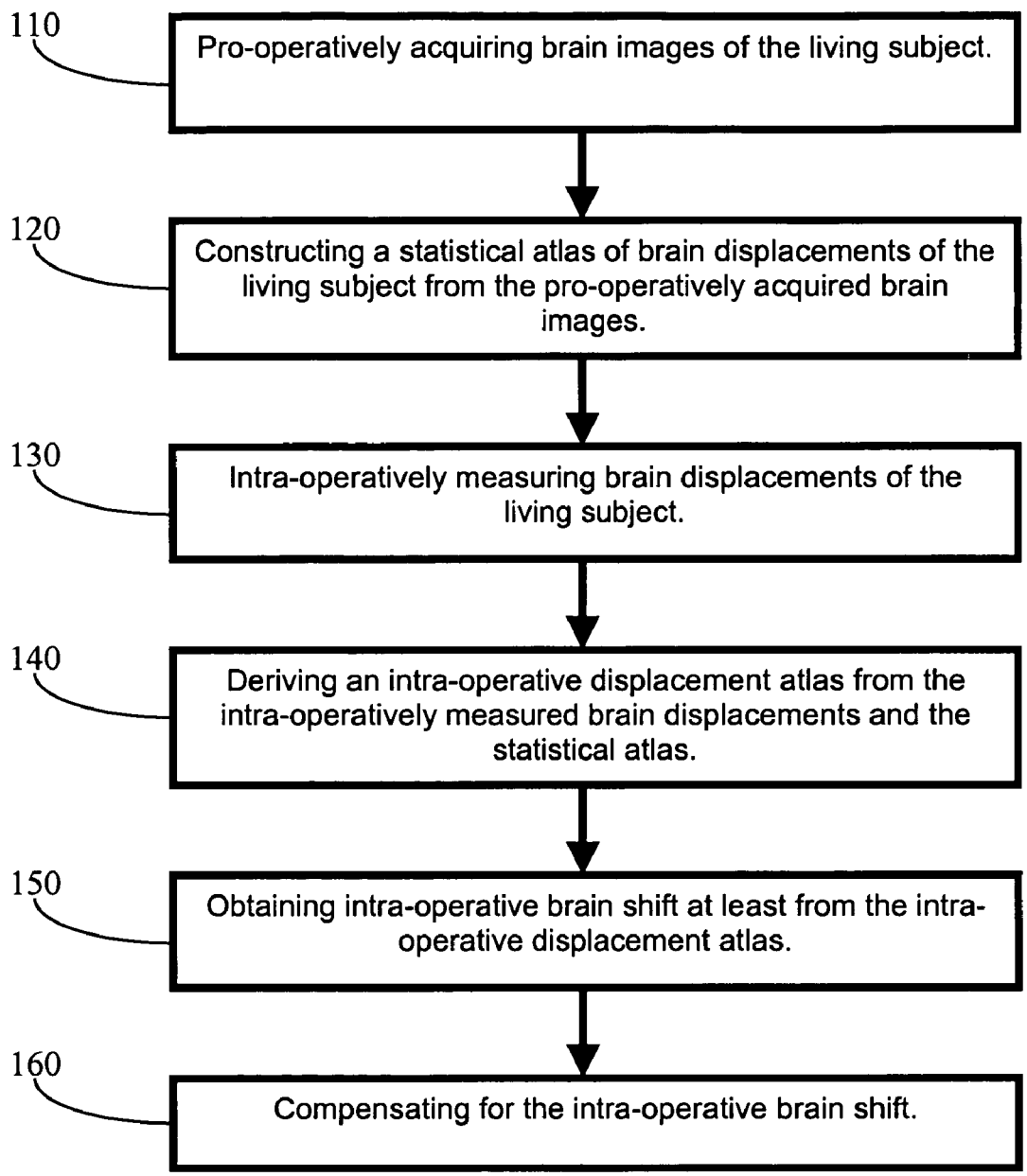
FIG. 1 is a flowchart for compensating for intra-operative brain shift of a living subject according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing pig.

As used herein, "brain shift," and "brain deformation" are synonyms in the specification.

Overview of the Invention

The present invention, in one aspect, relates to a method of compensation for intra-operative brain shift of a living subject. Referring in general to FIGS. 1–6, and first to FIG. 1, the method, according to one embodiment of the present invention, is schematically illustrated in a flow chart. At step 110, brain images of the living subject are pro-operatively acquired. The pro-operatively acquired brain images of the living subject comprise image data with respect to the brain surface geometry, where the image data with respect to the brain surface geometry is obtained through the use of at least one of positron emission tomography device, electroencephalography device, computer tomography device, functional magnetic resonance imaging device, magnetic resonance imaging device, and ultrasound imaging device.

Figure 2:
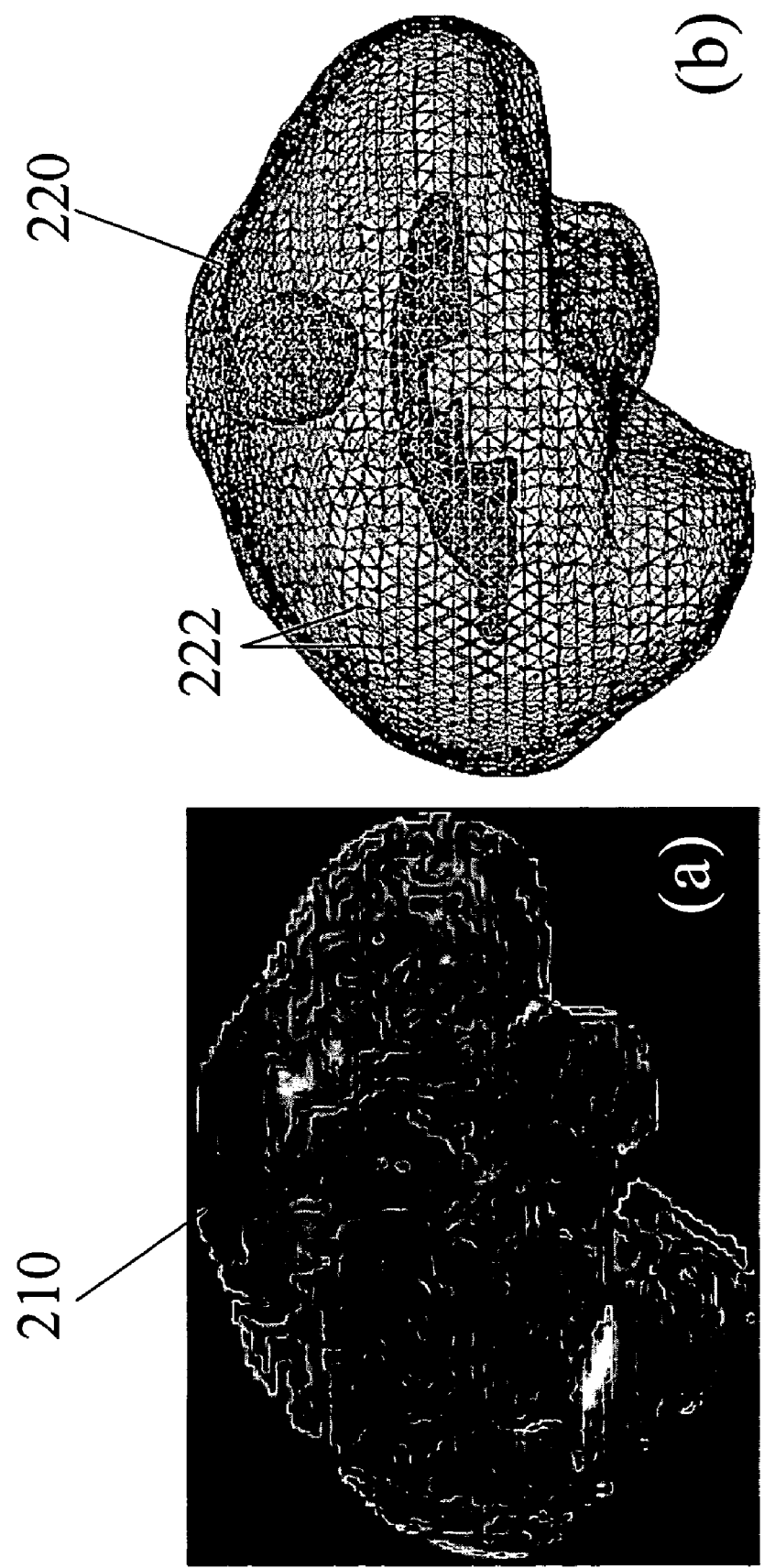
FIG. 2 shows (a) a pre-operative MRI surface rendering of the brain of a living subject, and (b) a corresponding finite element mesh with internal tumor and lateral ventricles visible generated from (a).

At step 120, a statistical atlas of brain displacements of the living subject is constructed from the pro-operatively acquired brain images, where the statistical atlas in one embodiment may be formed in the form of an n×m matrix, [E], with n, m being integers. In one embodiment, step 120 of constructing the statistical atlas [E] of brain displacements has the steps of obtaining m model solutions corresponding to a pre-operative surgical plan for the living subject using a finite element mesh having n nodes, and generating the statistical atlas [E] in the form of an n×m matrix with each model solution E, which is in the form of a n×1 matrix, forming a column of the matrix. In practice, the finite element mesh having n nodes is generated based on the pre-operative brain images through a series of mesh generation processes. For example, as shown in FIG. 2, image 210 was a MRI image pre-operatively acquired from the brain of a patient who bad developed a large contrast-enhanced right frontal lobe mass. Finite element mesh 220 having nodes 222 was generated from the pre-operative MRI image 210, by a computing software, such as ANALYZE AVW® (Mayo Clinic, Rochester, Minn.), or MATLAB® (Mathworks, Inc, Natick, Mass.).

The model solutions are obtained by solving the equations of:

$$\nabla \cdot G \nabla U + \nabla \frac{G}{1-2v}(\nabla \cdot U) - \alpha \nabla p + (\rho_t - \rho_f)g = 0, \quad (1)$$

$$\alpha \frac{\partial}{\partial t}(\nabla \cdot U) + \frac{1}{S}\frac{\partial p}{\partial t} - \nabla \cdot k \nabla p = 0, \quad (2)$$

at each of n nodes on the finite element mesh. In equations (1) and (2), U is a displacement vector, G is a shear modulus, v is a Poisson's ratio, p is an interstitial fluid pressure, α is a ratio of fluid volume extracted to volume change of the tissue under compression, k is a hydraulic conductivity, 1/S is an amount of fluid forced into the tissue under constant volume, $\rho_t$ is the density of tissue, $\rho_f$ is the density of fluid, and g is the gravitational acceleration vector. The equations (1) and (2), in one embodiment, can be solved numerically using the Galerkin weighted residual method. Finite element treatment of these equations coupled with a weighted time stepping scheme results in an equation of the form $$[A]\{U^{n+1}\}=B\{U^n\}+\{C^{n+\theta}\}, (0 \leq \theta \leq 1) \quad (3)$$

where [A] and [B] represent the stiffness matrices for the (n+1)-th and n-th time steps, respectively and {C} represents integrations of boundary integral expressions associated with the traditional "weak" forms of the weighted residual expression.

Figure 3:
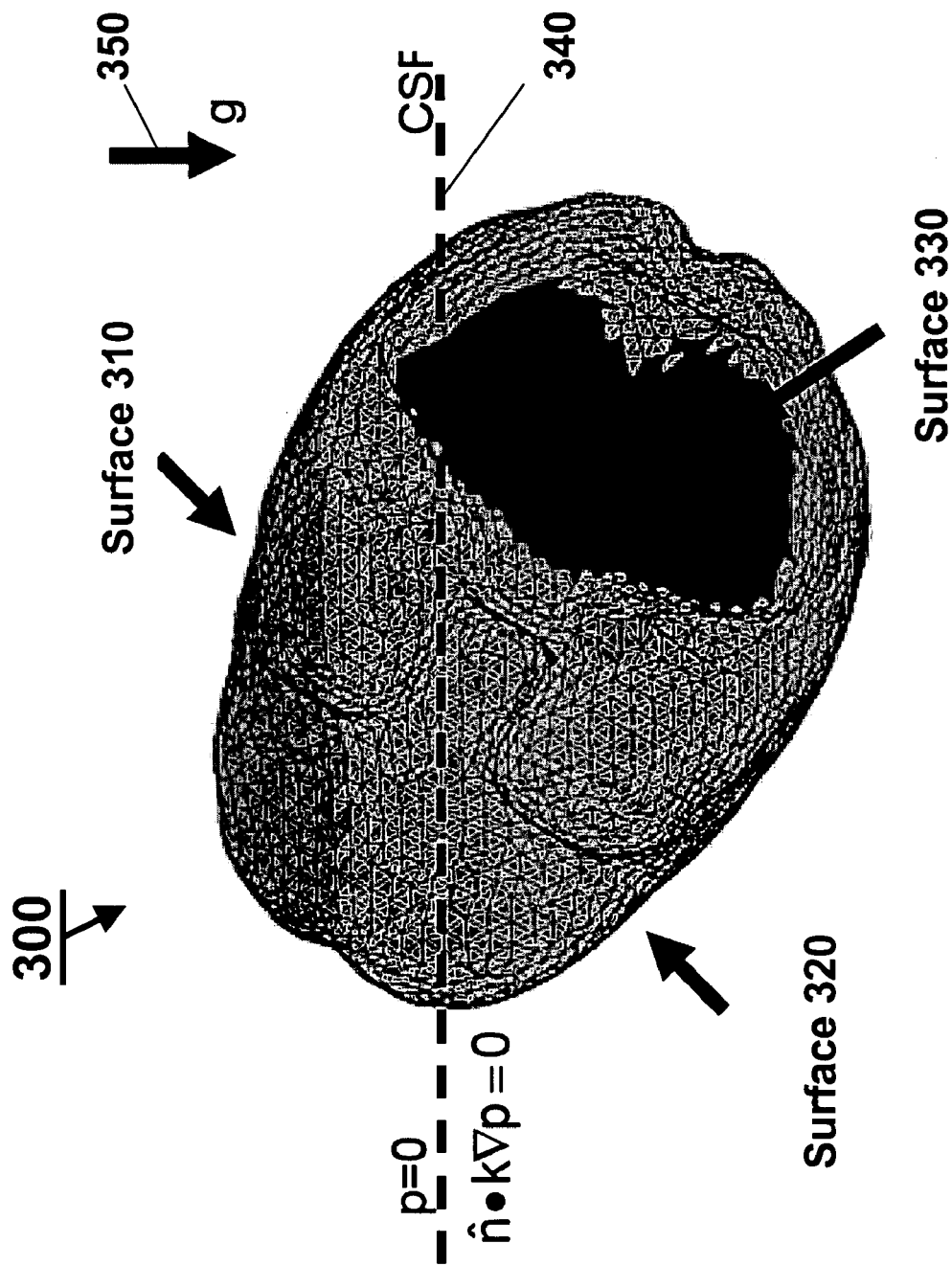
FIG. 3 shows a generalized boundary condition according to one embodiment of the present invention.

According to the model described by equations (1) and (2), the brain of a living subject can be considered as a biphasic continuum in which changes in hydration are directly coupled to changes in volumetric strain over time. When load is applied in the model, there is an instantaneous drainage at the contact area with subsequent movement over time depending on the flow of interstitial fluid. For the compensation for brain shift due to the distributed loading condition, such as gravity, a generalized form of the boundary conditions for the model is determined as a function of the living subject's head orientation and amount of cerebrospinal fluid (hereinafter "CSF") drainage of the brain of the living subject. Referring now to FIG. 3, a possible generalized geometric boundary condition configuration 300 for predicting brain shift of a living subject due to gravity is shown. In the boundary condition configuration 300, the highest elevations (Surface 310) in the brain are stress-free and allow drainage to the surface 310; the mid elevations (Surface 320) slide along the cranial wall and can experience partial drainage and the lowest elevations (Surface 330) allow movement along the cranial wall but do not allow fluid drainage. The orientation of the head of the living subject in relation to gravity determines the interface 340 (i.e. CSF drainage level) of Surface 310 and Surface 320 that is always orthogonal to the direction of gravity 350 and at an approximate level where the brain surface normal is nearly orthogonal with respect to the gravitational vector g. Surface 3 is usually designated in the brain stem region. The CSF drainage level (interface 340) shown in FIG. 3 has two roles: (1) to specify the interstitial pressure boundary conditions, and (2) to specify the region where buoyancy forces are no longer active.

In its current formulation, the only information required from the pre-operative surgical plan involves a general avenue for tumor approach and the anticipated orientation with respect to the direction of gravity, i.e. the anticipated patient fixation. Once the pre-operative surgical plan for the living subject is established, the orientation of the head of the living subject with respect to the gravity in the OR is anticipated and the CSF drainage level is predicted. The predicted level of intracranial CSF determines the fluid drainage boundary condition for the highest and mid elevations in the brain. Therefore, the boundary condition for solving the model can be determined. Considering that the pre-operative plan is not exactly achieved, a range of surgical simulations is performed which vary the patient orientation in a fixed range about the anticipated orientation. In addition, different levels of buoyancy force interaction are also simulated, i.e. the degree of sag from the brain's weight as CSF is lost. Once the ranges are designated all simulations are conducted in parallel on a standard computer cluster prior to surgery. To generate a statistical atlas [E] of brain displacement, the boundary condition for solving the model therefore is designated as a range of orientations of the head of the living subject with respect to the direction of gravity and amounts of CSF drainage of the brain of the living subject. By varying the CSF level (interface 340) and the head orientation with respect to gravity, the geometric description changes and each precipitated solution of the model becomes parts of the statistical atlas of brain displacements for the living subject. In one embodiment, the statistical atlas [E] is in the form of $$[E]=\{E_{ij}\}=\begin{bmatrix} U_1^1 & U_1^2 & \cdots & \cdots & U_1^m \\ U_2^1 & U_2^2 & \cdots & \cdots & U_2^m \\ \cdots & \cdots & \cdots & \cdots & \cdots \\ \cdots & \cdots & \cdots & \cdots & \cdots \\ U_n^1 & U_n^2 & \cdots & \cdots & U_n^m \end{bmatrix}, \quad (4)$$

where $E_{ij}=U_i^j$ is a brain displacement value for i-th nodal position on the finite element mesh at the j-th orientation and cerebrospinal fluid drainage level, and where $1 \leq i \leq n$, and $1 \leq j \leq m$. The statistical atlas of brain displacements is spatially and temporally sensitive.

Figure 4:
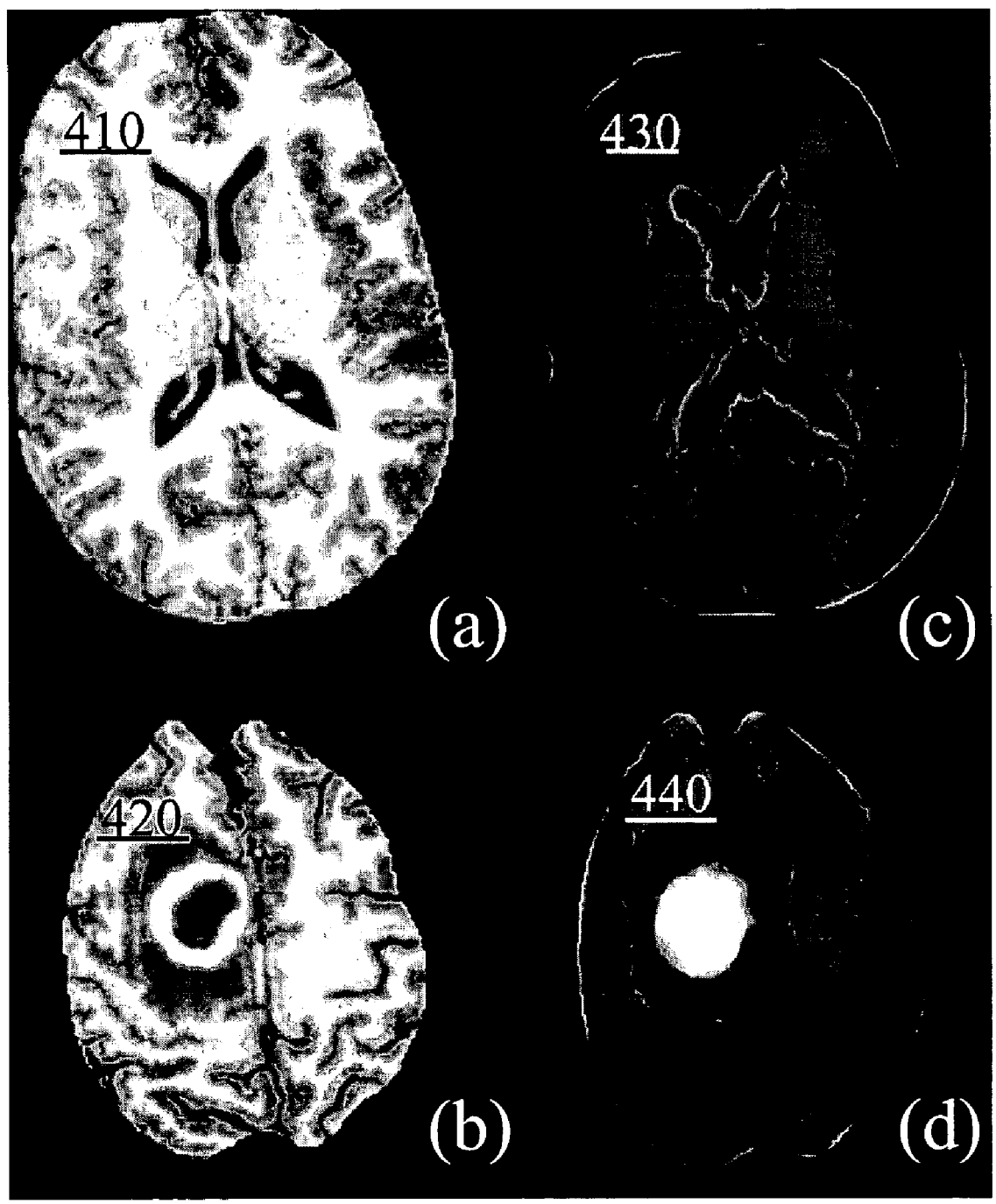
FIG. 4 shows (a) and (b) pre-operative MRI axial slices different location within the brain of the living subject of FIG. 2, and (c) and (d) model material property distributions corresponding to (a) and (b), respectively.

Additionally, specific structures of the brain of the living subject can be incorporated in the boundary conditions for solving equations (1) and (2). For example, the specific structures of the brain of the living subject include at least one of a falx cerebri, tentorium cerebelli, lateral ventricle, white matter, gray matter, tumor, edema-induced swelling, mannitoi-induced shrinking, and any combination thereof. FIG. 4 shows MRI axial slices 410 and 420 pre-operatively acquired at different location within the brain of the patient who had developed a large contrast-enhanced right frontal lobe mass, as shown in FIG. 2, and corresponding model material property distributions 430 and 440, respectively. The material properties for the brain of a living subject at least include variables such as G, ν, α and 1/S in equations (1) and (2).

Referring back to FIG. 1, at step 130, brain displacements of the living subject are intra-operatively measured, which in one embodiment can be in the form of a n×1 matrix, {f}. Step 130 of measuring intra-operative brain displacements is performed with a scanning device that is capable of obtaining frequency, intensity and geometric data with respect to the cortical surface of the living subject simultaneously. In one embodiment, the scanning device includes an ultrasound imaging device. In another embodiment, the scanning device includes a laser range scanner (hereinafter "LRS"), for example, RealScan3D, (3D Digital Corporation, Bedford Hills, N.Y.). The RealScan3D is lightweight, compact, and has a standard tripod mount with a volume 9.5"×12.51"× 3.25" and weight 4.5 lbs. For a clinical use, the RealScan3D is equipped with a customized vibration-damping monopod, and/or attached to a surgical arm within the OR. The scanning field of the RealScan3D has 512 horizontal points by 500 vertical points per scan and is accomplished in approximately 5 s to 7 s. The laser used in the LRS is a Class-I "eye-safe" 6.7 mW visible laser. The laser stripe generator has an adjustable fan-out angle (maximum fan-out is 30°) and acquires each stripe at approximately 60 Hz. The LRS accuracy is 300 μm at a position that is 30 cm far from a targeted region of interest and approximately 1000 μm at a position that is 80 cm far from the targeted region of interest. Other types of LSRs can also be used to practice to the present invention. The ability to rapidly capture both geometric and color-intensity information from an intra-operative brain surface has made LRS to be a preferable tool for measuring brain displacements. In addition, various types of scanning devices for digitizing and tracking cortical features, such as a Surgiscope sterrotactic system (Elekta AB, Stockholm, Sweden), or a video imaging device, can be utilized to intra-operatively measure brain displacements of a living subject [28]. Thus, these devices can also be used to practice the current invention alone or in combination.

At step 140, an intra-operative displacement atlas $[X_f]$ is derived from the intra-operatively measured brain displacements $\{f\}$ and the statistical atlas $[E]$, where $[X_f]$ is a n×m matrix containing the brain displacements for all points in the brain of the living subject at the various orientations and CSF drainage levels.

At step 150, intra-operative brain shift is obtained at least from the intra-operative displacement atlas $[X_f]$. In one embodiment, the step of obtaining the intra-operative brain shift has the steps of minimizing the function $\|[E]\{x\}-\{f\}\|$ subject to $\{x\} \geq 0$, so as to obtain regression coefficients $\{x\}$, where the sum of the regression coefficients $\{x\}$ is subject to unity, and calculating the intra-operative brain shifts of the living subject from the following relation:

$$\{\text{Intra-operative brain shift}\}=[X_f]*\{x\}, \quad (5)$$

where $\{x\}$ are the regression coefficients obtained in the minimizing step. The minimizing step, in one embodiment, is performed with a least-squares regression algorithm.

And at step 160, the intra-operative brain shift is compensated for by updating the pre-operatively acquired images of the living subject with the intra-operatively measured brain displacements. During the course of surgery for the living subject, various technologies such as laser range scanning can be used to measure the brain surface displacements. The displacements can be compared to the predicted displacements of the statistical atlas and used within the context of a statistical model to construct a solution that best fits the measured brain displacements. Once the best-fit displacement field is determined, the images are updated and the surgeon can go forward.

In addition to simulation of the effect of the distributed loading conditions that are associated with gravity, edema-induced swelling, mannitoi-induced shrinking, and the likes, on brain shift of a living subject, as described above, the model described by equations (1) and (2) can also be used to effectively model the effect of the surface-based loading conditions that are associated with tissue retraction, tissue resection, and the likes, on brain shift of the living subject.

In one embodiment, processing of the pre-operative acquired brain images, intra-operatively measured brain displacements, atlas construction, and model updating are performed with a computer or a computer cluster. The computational results are then displayed on a display in the OR for surgical use.

These and other aspects of the present invention are further described below.

METHODS, IMPLEMENTATIONS AND EXAMPLES OF THE INVENTION

Without intend to limit the scope of the invention, further exemplary procedures and preliminary experimental results of the same according to the embodiments of the present invention are given below.

Example 1

Animal Experiment

To evaluate the accuracy and effectiveness of the computational model for predicting of brain deformations, in vivo experiments were conducted with a porcine. In these experiments, a porcine brain was implanted with small CT-visible markers in a grid-like fashion using a needle. Following implantation, a series of gradual deformations consistent with neurosurgical loading rates were applied and recorded using the CT. By recording the bead positions in each image volume, a complete subsurface trajectory for all deformation stages was determined. Following the experiment, subject-specific finite element models of all test subjects were constructed from the pre-operative MR and registered to the CT data set. Deformations applied in the OR were now applied in simulation and bead trajectories were compared to ascertain model-predictive fidelity. In addition to uni-axial deformations, validation with realistic loading conditions such as from the retraction of tissue were investigated.

TABLE 1

Results from series of piston experiments under 4, 8, 10, 12, 14 mm of piston motion, remaining average bead displacement error after model-compensation, and the average bead displacement, respectively.

| Device Displacement (mm) | Remaining Displacement Error (mm) | | Bead Displacement (mm) | |
|---|---|---|---|---|
| | Average | Maximum | Average | Maximum |
| 4 | 0.3 ± 0.2 | 0.9 | 1.2 ± 0.7 | 3.3 |
| 8 | 0.4 ± 0.3 | 1.2 | 2.5 ± 0.7 | 5.5 |
| 10 | 0.4 ± 0.3 | 1.3 | 3.2 ± 1.6 | 6.8 |
| 12 | 0.5 ± 0.4 | 1.7 | 3.9 ± 2.0 | 8.2 |
| 14 | 0.6 ± 0.4 | 2.0 | 4.4 ± 2.2 | 8.7 |

Table 1 represents example results from a 3 subject experiment set, the first column corresponds to the results from a series of piston experiments under 4, 8, 10, 12, 14 mm of piston motion, respectively, the second column represents remaining average bead displacement error after model-compensation, and the third column corresponds to the average bead displacement. The results of all studies indicated about 70% to 80% capturing of subsurface motion.

Example 2

Clinical Trials

In one embodiment of the present invention, four patients who undergo brain surgery were chosen to gather data for evaluating the invented method. The four patients were employed merely as an example to acquire data for practicing the present invention, and the use of the four patients should not limit the scope of the present invention. Each patient was assigned a number from Patent 1 to Patient 4 as his or her identification. Additionally, prior to clinical data acquisition, the surgical procedures for human patients were approved by the Vanderbilt University Institutional Review Board (hereinafter "VUIRB") and patient consent was acquired for all clinical data.

In four clinical cases studying the effects of gravity-induced brain sag, features on the cortical surface (i.e. blood vessel bifurcations) were digitized and tracked in the OR in the direction of gravity. The cases involved 4 supine cases with 2 patients having the head in the neutral position and 2 cases having the head rotated to the right 60 degrees. Clinical data acquisitions for the four patients are highlighted as follows.

Patient 1 was a 35-year-old male having a history of medically intractable epilepsy, associated with a posterior orbito-frontal tumor. Electrode strip recordings identified that he had a tumor surrounded with epileptogenic cortex. He was brought to the OR for resection of the tumor and the surrounding epileptogenic cortex. At the time of surgery the patent was administered with general anesthesia and was supine with the head secured in three-point fixation and turned 60° to his right.

Patient 2 was a 33-year-old man who had previously undergone resection of a left frontal lobe arteriovenous malformation and then presented with a medically intractable seizure disorder. MRI revealed that he had encephalomalacia in the area of the left gyrus rectus and orbito-frontal cortex. He was brought to the OR for resection of this cortex and associated gliotic scar. He was under general anesthesia and positioned supine with the head turned 60° to his right and secured with a Mayfield clamp. The previous bicoronal bone flap was opened on the left side and dissection was carried out from the lateral fronto-orbital cortex medially.

Patient 3 was an 18-year-old female with a long-standing medically intractable, MRI-negative seizure disorder. The patent had undergone intracranial electrode investigation without satisfactory localization of seizure onset. She was brought to the OR for anterior ¾ corpus callosal section. Under general anesthesia, she was positioned supine with her head in neutral position in three-point pin fixation. A right parasagittal frontal craniotomy and retraction of the right hemisphere allowed visualization down the interhemispheric fissure to the corpus callosum. The commissural section was performed with a blunt dissector and suction.

Patient 4 was a previously healthy 54-year-old woman who developed the acute onset of left-sided weakness and was found to have a large contrast-enhancing right frontal lobe mass by CT and MRI scans. A right frontal craniotomy was performed with the patient supine under general anesthesia and the head secured unturned in three-point pin fixation. A gross total resection of the enhancing mass was accomplished; the histopathologic diagnosis was glioblastoma multiforme.

In each case, there was minimal surgical intervention immediately-post craniotomy but significant CSF drainage. A patient-specific model mesh was generated for each patient from the pre-operatively acquired MRI data set, where the model mesh contained about 15,000 to 17,000 nodes, which yielded a typical spacing of 0.5 cm on the mesh. Tissue mechanical properties were based on previous pig brain experiments [29] that investigated consolidation theory modeling in vivo, as described above. These values were within a physiologically reasonable range, given the limited amount of in vivo data that is available on the human brain. They were softer than those used in the Nagashima studies [47], but more in keeping with the estimates by Basser based on analytical analyses [50]. The gravitational acceleration vector was determined from OR information on the patient orientation, and the CSF was defined to cover the lower portion of the brain, depending on the position of the cranial opening. FIG. 3 illustrates the boundary conditions used in the model for a surgical orientation, i.e., 60° to patient's right. Although the actual conditions applied were case specific, generally, the highest elevations in the brain (Surface 310) resided at atmospheric pressure and were stress free, the mid-elevations (Surface 320) slide along the cranial wall but were restricted in their normal direction (to the cranium) movement, the brain stem area is fixed at atmospheric pressure, while the lowest elevations (Surface 330) were similar to the mid-elevations but did not allow fluid drainage. The CSF fluid-line was typically located along interface 340 of Surface 310 and Surface 320.

Although the above intra-operative data is sparse, a laser ranger scanner significantly improved the number of measured data points and hence should constrain and aid the statistical model. To simulate this, for each patient, a specific orientation and CSF level were selected which were not to be part of the statistical solution set. In all cases, the computational model was executed for a range of patient orientations and CSF drainage states. The coefficients were then calculated using the statistical model and intra-operative brain shift was compared to the model solution not included within the statistical set. The results were presented in the following section.

The results of the statistical model and the measured displacements were shown in Table 2. In Table 2, each row in the first column corresponds to a patient undergoing brain surgery, each number in the second column identified a position (landmarker) for measuring brain displacement at the position for a specific patent. The values in the third column and the fourth column were based on the findings of a computational model [28]. The fifth column indicated the statistical model prediction on a point-by-point basis. Point 3 in Patients 3 and 4 was on bone and hence experienced.

TABLE 2

Measured brain displacements, computational model predicted brain displacements and statistical model predicted brain displacements with respect to gravity.

| Subject | Point Number | Measured Displacement (mm) | Computational Model Displacement (mm) | Statistical Model Displacement (mm) |
|---|---|---|---|---|
| Patient 1 | 1 | 6.7 | 4.9 | 4.7 |
| | 2 | 4.6 | 5.4 | 5.1 |
| | 3 | 4.2 | 5.8 | 5.4 |
| | 4 | 3.5 | 3.4 | 3.6 |
| Patient 2 | 1 | 10.4 | 5.7 | 7.4 |
| | 2 | 6.2 | 6.3 | 7.2 |
| | 3 | 5.9 | 6.2 | 7.8 |
| Patient 3 | 1 | 6.1 | 5.2 | 4.8 |
| | 2 | 5.0 | 6.5 | 6.2 |
| | 3 | N/A | N/A | N/A |
| | 4 | 7.5 | 6.1 | 5.9 |
| Patient 4 | 1 | 4.4 | 4.8 | 4.5 |
| | 2 | 3.5 | 3.8 | 3.4 |
| | 3 | N/A | N/A | N/A |

Averaging over all points in the four patient cases, the statistical model produces an absolute error of about 1.1±0.9 mm. For the computational model, an average error of about 1.2±1.3 mm was reported. The statistical model predicts approximately 75% to 80% of the intra-operative brain shift.

TABLE 3

Maximum and mean errors generated by the statistical model for the simulated intra-operative data acquisition.

| Subject | Maximum Error (mm) | Mean Error (mm) |
|---|---|---|
| Patient 1 | 1.9 | 0.2 |
| Patient 2 | 0.3 | 0.06 |

TABLE 3-continued

Maximum and mean errors generated by the statistical model
for the simulated intra-operative data acquisition.

| Subject | Maximum Error (mm) | Mean Error (mm) |
|---|---|---|
| Patient 3 | 0.4 | 0.07 |
| Patient 4 | 0.3 | 0.07 |

The results of the statistical model for the simulation were shown in Table 3. The values in the second column corresponded to the maximum difference between the measured intra-operative brain displacements and those predicted by the statistical model. In a similar fashion the values in the third column represented the mean error. Averaging over all points in the four patient cases, the statistical model produced an absolute maximum error of about 0.7±0.8 mm and a mean error of about 0.1 mm±0.08 mm. Relative to the average cortical displacement of about 2.4 mm, the statistical model predicted an average error of about 0.1 mm, indicating that it recaptured about 96% of the simulated intra-operative brain shift.

The statistical model performed comparably to the results reported in [28] and was able to compensate for about 75% to 80% of brain shift. To increase the accuracy, simulations suggest that dense intra-operative cortical shift measurements may be appropriate. In the simulation case reported, the statistical model results in an average error of about 0.1 mm displacement error and predicts approximately 96% of the intra-operative brain shift.

With the advent of cost-effective and efficient intra-operative data acquisition techniques such as laser range scanning, the statistical model can prove to be a useful tool for model updated image guidance. Furthermore, the statistical model should significantly reduce intra-operative computational time since perturbations of patient orientation and the state of CSF drainage can be pre-computed.

Figure 5:
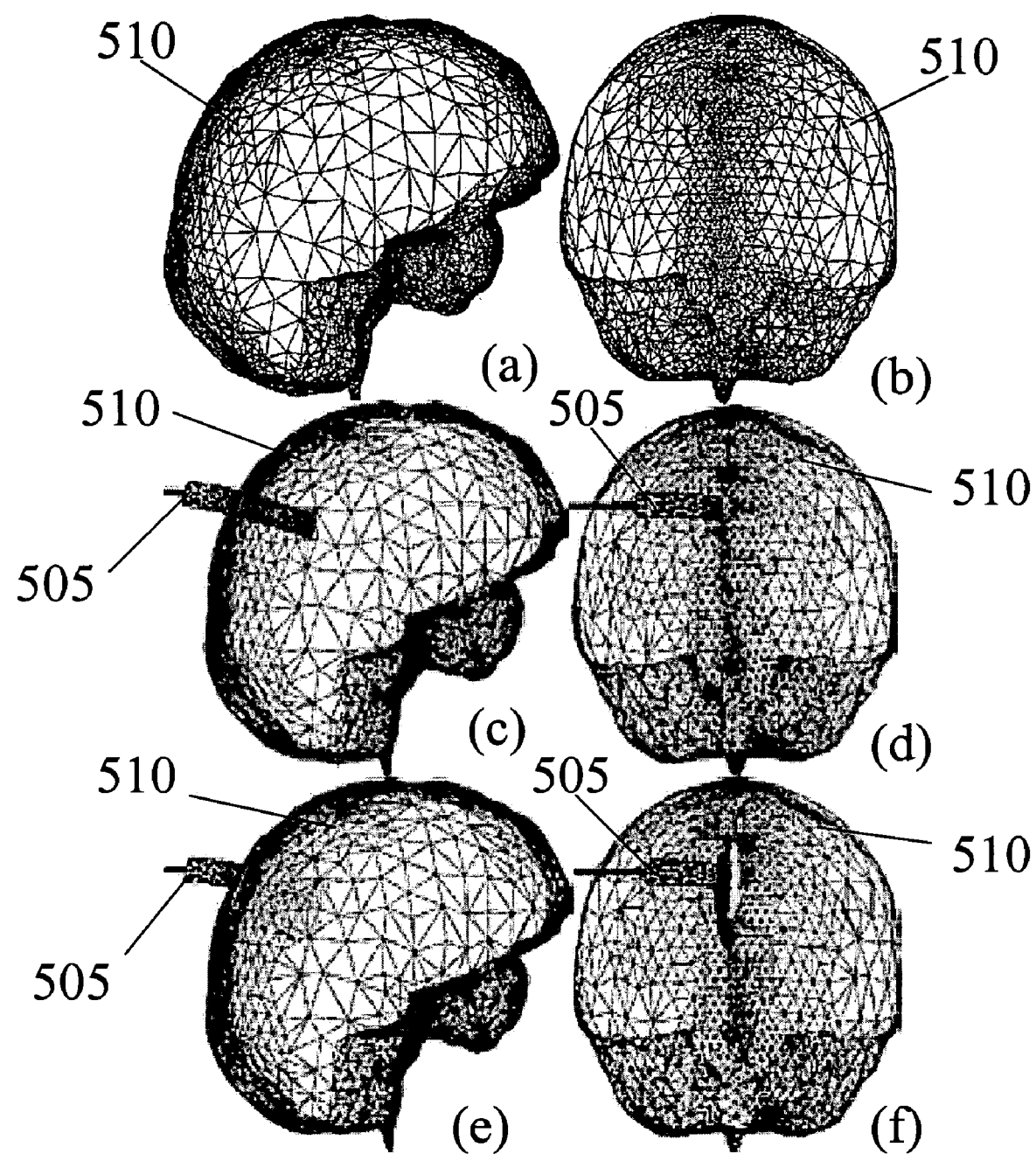
FIG. 5 shows steps in a three-dimensional numerical retraction according to one embodiment of the present invention: (a) and (b) generation of the tetrahedral grid in different views, with refinement around the surgical trajectory, (c) and (d) arbitrary placement of a retractor in the computational domain on the tetrahedral grid in different views, and (e) and (f) classification, segmentation, and separation of elements about the retractor plane on the tetrahedral grid in different views.

The present invention, in one aspect, also relates to a method of compensation for brain shift that is resulted from surface-based loading conditions associated with tissue retraction and tissue resection. The computational procedures to implement tissue retraction and tissue resection disclosed in the current invention allow the arbitrary insertion of retractors and removal of tissue with the brain of a living subject. An example of three dimensional retractor deployment within the computational model is shown in FIG. 5. At first, a tetrahedral grid 510 is generated with refinement around the surgical trajectory, as shown in FIGS. 5a and 5b. Then, retractor 505 is placed in the tetrahedral grid 510, as shown in FIGS. 5c and 5d. Thirdly, as shown in FIGS. 5e and 5f, classification, segmentation, and separation of elements are performed about the retractor plane.

Figure 6:
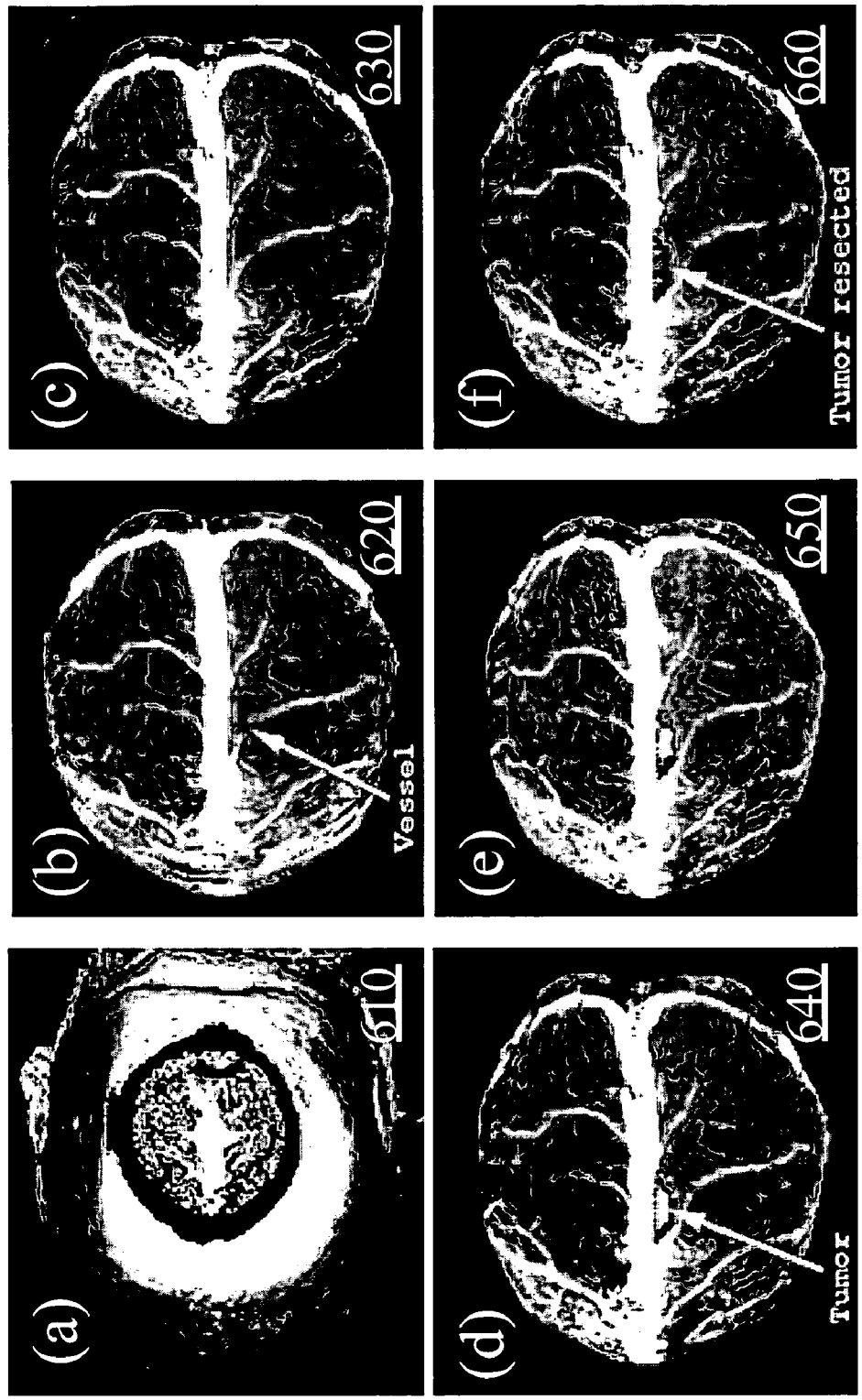
FIG. 6 shows volume-rendered, high-resolution, preoperative images deformed by modeling of intra-operative surgical conditions according to one embodiment of the present invention: (a) preoperative patient orientation, (b) preoperative brain surface with identification of the vessel, (c) after the onset of gravitational sag, (d) after retraction, with tumor identification, (e) after partial tumor resection, and (f) after complete tumor removal, with the brain still in the retracted position.

These procedures have been thoughtfully designed so re-meshing does not need to be performed. Preliminary results from a complete clinical case simulation where a tumor near the falx was removed is outlined as follows. The clinic data were acquired from a 60-year-old male with metastatic non-small cell carcinoma, which presented as a left frontopartial mass. FIG. 6 showed a sequence of pre-operative and model updated image volumes that indicate the important neurosurgical events occurred during surgery. On the basis of intra-operatively acquired photographs and patient registration information, the preoperative MRI data were volume rendered in the approximate OR position and orientation (610). The prominent vessel was localized on the segmented brain (620). Gravity was applied, and the image was volume-updated accordingly (630). By using the optical images from the operating microscope and cortical features such as the surface vasculature for retractor localization, the model-updated MRI representation after retraction was then produced (640). Resection techniques were applied, and the image volume was redisplayed after partial and complete tumor removal (650 and 660, respectively).

Further Discussions

In the present invention, among other things, a statistical based approach has been disclosed for image-guided surgery. The approach is capable of accounting for: (1) brain deformation of a living subject, (2) interstitial pressure gradients of the brain of a living subject, (3) gravity effects on brain deformation of a living subject, (4) drug effects on brain deformation of a living subject, and (5) capillary-to-tissue fluid exchange in the brain of a living subject. The statistical model was compared with measured intra-operative data and with a simulated intra-operative case. These simulations showed a good match between the brain shifts predicted by the computational model and that predicted by the statistical model. Given the prominent role that gravity takes in the development of brain shift, it is encouraging that a relatively simple statistical model increases the model-updating speed by providing a framework to pre-compute the early stages of brain shift and can also be used to compensate for this motion. Computationally efficient strategies to account for modeling retraction and resection have also been developed. Specifically, to simulate retraction and resection, a multi-step process has been developed which allows for the arbitrary orientation, and movement of a retractor and removal of tissue without the need for regenerating the patient computer model.

Although the current model is of significant sophistication, the rationale for developing better models to simulate the deformation behavior in the brain is self-evident, e.g. tumor growth, hydrocephalus, edema, convective therapy, etc. It has been found that over the course of surgery the brain can relax (not shown here). This relaxation phenomenon is not currently incorporated within the model described in equations (1) and (2). Although this behavior is not anticipated to be a first order influencing event, understanding the relaxation physics could be important when dealing with the second stage events, for example, how does the relaxation affect tumor boundaries during retraction?

In addition to constitutive behavior of the computational model (i.e., the incorporation of a different model to represent brain deformation mechanics), other improvements to the statistical atlas approach may need to be addressed. An example would be the work of Davatzikos [44], which used a shape-based statistical model. In this work, a geometric shape and its deformed states are parameterized by a vector mean, $\{\mu\}$, and covariance matrix, $[C]$. If $\{V\}$ denotes a distribution of eigenvectors of $[C]$ then the shape of the geometry, $\{x\}$, can be expressed as in equation (6) as follows:

$$\{x\} = \{\mu\} + \sum_{i=1}^{M} \alpha_i V_i. \tag{6}$$

In the context of the present invention, the deformation data acquired by the various orientations and drainage levels as provided by the model may serve as the training set and allow the calculation of the mean and covariance. This information may be used as a statistical prior to iterate on eigenvector combinations as provided by of that best matches the measured shape change as provided by the textured LRS measurement system. This extension will be compared to the model to determine the best method for the pre-computation strategy for body-based loading conditions.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] C. R. Maurer, J. M. Fitzpatrick, M. Y. Wang, R. L. Galloway, R. J. Maciunas, and G. S. Allen, "Registration of head volume images using implantable fiducial markers," *IEEE Trans. Med. Imag.*, vol. 16, pp. 447–462, April 1997.

[2] J. M. Fitzpatrick, D. L. G. Hill, and C. R. Maurer, *Handbook of Medical Imaging*, M. Sonka and J. M. Fitzpatrick, Eds. Bellingham, Wash.: SPIE Press, 2000, vol. 2, pp. 447–513.

[3] W. E. L. Grimson, G. J. Ettinger, S. J. White, T. Lozano Perez, W. M. Wells, and R. Kikinis, "An automatic registration method for frameless stereotaxy, image guided surgery, and enhanced reality visualization," *IEEE Trans. Med. Imag.*, vol. 15, pp. 129–140, February 1996.

[4] C. R. Maurer, R. J. Maciunas, and J. M. Fitzpatrick, "Registration of head CT images to physical space using a weighted combination of points and surfaces," *IEEE Trans. Med. Imag.*, vol. 17, pp. 753–761, May 1998.

[5] M. A. Audette, K. Siddiqi, and T. M. Peters, "Level-set surface segmentation and fast cortical range image tracking for computing intra-surgical deformations," in *Lecture Notes in Computer Science*. New York: Springer-Verlag, 1999, vol. 1679, Medical Image Computing and Computer Assisted Intervention: MICCAI'99, pp. 788–797.

[6] A. J. Herline, J. L. Herring, J. D. Stefansic, W. C. Chapman, R. L. Galloway, and B. M. Dawant, "Surface registration for use in interactive image-guided liver surgery," in *Lecture Notes in Computer Science*. New York: Springer-Verlag, 1999, vol. 1679, Medical Imaging Computation and Computer-Assisted Intervention: MICCAI'99, pp. 892–899.

[7] A. Raabe, R. Krishnan, R. Wolff, E. Hermann, M. Zimmermann, and V. Seifert, "Laser surface scanning for patient registration in intracranial image-guided surgery," *Neurosurgery*, vol. 50, no. 4, pp. 797–801, 2002.

[8] M. A. Audette, F. P. Ferrie, and T. M. Peters, "An algorithmic overview of surface registration techniques for medical imaging," *Med. Image Anal.*, vol. 4, no. 3, pp. 201–217, 2000.

[9] R. L. Galloway, "The process and development of image-guided procedures," *Annu. Rev. Biomed. Eng.*, vol. 3, pp. 83–108, 2001.

[10] P. J. Kelly, B. Kall, S. Goerss, and F. I. Earnest, "Computer-assisted stereotaxic laser resection of intra-axial brain neoplasms," *J. Neurosurg.*, vol. 64, pp. 427–439, 1988.

[11] H. J. Nauta, "Error assessment during "image guided" and "imaging interactive" stereotactic surgery," *Comput. Med. Imag. Graphics*, vol. 18, no. 4, pp. 279–287, 1994.

[12] D. L. G. Hill, C. R. Maurer, R. J. Maciunas, J. A. Barwise, J. M. Fitzpatrick, and M. Y. Wang, "Measurement of intra-operative brain surface deformation under a craniotomy," *Neurosurgery*, vol. 43, no. 3, pp. 514–526, 1998.

[13] D. W. Roberts, A. Hartov, F. E. Kennedy, M. I. Miga, and K. D. Paulsen, "Intra-operative brain shift and deformation: A quantitative analysis of cortical displacement in 28 cases," *Neurosurgery*, vol. 43, no. 4, pp. 749–758, 1998.

[14] L. D. Lunsford, R. Parrish, and L. Albright, "Intra-operative imaging with a therapeutic computed tomographic scanner," *Neurosurgery*, vol. 15, no. 4, pp. 559–561, 1984.

[15] C. Nimsky, O. Ganslandt, S. Cerny, P. Hastreiter, G. Greiner, and R. Fahlbusch, "Quantification of, visualization of, and compensation for brain shift using intra-operative magnetic resonance imaging," *Neurosurgery*, vol. 47, no. 5, pp. 1070–1079, 2000.

[16] A. Nabavi, P. M. Black, D. T. Gering, C. F. Westin, V. Mehta, R. S. Pergolizzi, M. Ferrant, S. K. Warfield, N. Hata, R. B. Schwartz, W. M. Wells, R. Kikinis, and F. A. Jolesz, "Serial intra-operative magnetic resonance imaging of brain shift," *Neurosurgery*, vol. 48, no. 4, pp. 787–797, 2001.

[17] P. M. Black, T. Moriarty, E. Alexander, P. Stieg, E. J. Woodard, P. L. Gleason, C. H. Martin, R. Kikinis, R. B. Schwartz, and F. A. Jolesz, "Development and implementation of intra-operative magnetic resonance imaging and its neurosurgical applications," *Neurosurgery*, vol. 41, no. 4, pp. 831–842, 1997.

[18] C. Nimsky, O. Ganslandt, H. Kober, M. Buchfelder, and R. Fahlbusch, "Intra-operative magnetic resonance imaging combined with neuronavigation: A new concept," *Neurosurgery*, vol. 48, no. 5, pp. 1082–1091, 2001.

[19] W. E. L. Grimson, R. Kikinis, F. A. Jolesz, and P. M. Black, "Imageguided surgery," *Sci. Amer.*, vol. 280, no. 6, pp. 62–69, 1999.

[20] C. Nimsky, O. Ganslandt, P. Hastreiter, and R. Fahlbusch, "Intra-operative compensation for brain shift," *Surg. Neurol.*, vol. 56, no. 6, pp. 357–364, 2001.

[21] M. Knauth, N. Aras, C. R. Wirtz, A. Dorfler, T. Engelhorn, and K. Sartor, "Surgically induced intracranial contrast enhancement: Potential source of diagnostic error in intra-operative mr imaging," *Amer. J. Neuroradiol.*, vol. 20, no. 8, pp. 1547–1553, 1999.

[22] G. R. Sutherland, T. Kaibara, C. Wallace, B. Tomanek, and M. Richter, "Intra-operative assessment of aneurysm clipping using magnetic resonance angiography and diffusion-weighted imaging: Technical case report," *Neurosurgery*, vol. 50, no. 4, pp. 893–897, 2002.

[23] R. D. Bucholz, D. D. Yeh, J. Trobaugh, L. L. McDurmont, C. D. Sturm, C. Baumann, J. M. Henderson, A. Levy, and P. Kessman, "The correction of stereotactic inaccuracy caused by brain shift using an intra-operative ultrasound device," in *Lecture Notes in Computer Scien-* ce. New York: Springer-Verlag, 1997, vol. 1205, CVRMEDL: MRCAS'97, pp. 459–466.

[24] D. G. Gobbi, R. M. Comeau, and T. M. Peters, "Ultrasound/mri overlay with image warping for neurosurgery," in *Lecture Notes in Computer Science*. New York: Springer-Verlag, 2000, vol. 1935, Medical Image Computing and Computer-Assisted Intervention: MICCAI'00, pp. 106–114.

[25] A. Gronningsaeter, A. Kleven, S. Ommedal, T. E. Aarseth, T. Lie, F. Lindseth, T. Lango, and G. Unsgard, "Sonowand, an ultrasound-based neuronavigation system," *Neurosurgery*, vol. 47, no. 6, pp. 1373–1379, 2000.

[26] F. Lindseth, T. Lango, J. Bang, and T. A. N. Hernes, "Accuracy evaluation of a 3D ultrasound-based neuronavigation system," *Comput. Assist. Surg.*, vol. 7, pp. 197–222, 2002.

[27] D. W. Roberts, M. I. Miga, A. Hartov, S. Eisner, J. M. Lemery, F. E. Kennedy, and K. D. Paulsen, "Intra-operatively updated neuroimaging using brain modeling and sparse data," *Neurosurgery*, vol. 45, no. 5, pp. 1199–1206, 1999.

[28] M. I. Miga, K. D. Paulsen, J. M. Lemery, S. D. Eisner, A. Hartov, F. E. Kennedy, and D. W. Roberts, "Model-updated image guidance: Initial clinical experiences with gravity-induced brain deformation," *IEEE Trans. Med. Imag*, vol. 18, pp. 866–874, October 1999.

[29] M. I. Miga, K. D. Paulsen, F. E. Kennedy, P. J. Hoopes, A. Hartov, and D. W. Roberts, "In vivo analysis of heterogeneous brain deformation computations for model-updated image guidance," *Comput. Methods Biomech. Biomed. Eng.*, vol. 3, no. 2, pp. 129–146, 2000.

[30] R. Bajcsy, R. Lieberson, and M. Reivich, "A computerized system for the elastic matching of deformed radiographic images to idealized atlas images," *J. Comput. Assist. Tomogr.*, vol. 7, no. 4, pp. 618–625, 1983.

[31] J. C. Gee, D. R. Haynor, L. LeBriquer, and R. K. Bajcsy, "Advances in elastic matching theory and its implementation," in *Lecture Notes in Computer Science*. New York: Springer-Verlag, 1997, vol. 1205, CVRMed: MRCAS'97, pp. 63–72.

[32] G. E. Christensen, R. D. Rabbitt, and M. I. Miller, "3D brain mapping using a deformable neuroanatomy," *Phys. Med. Biol.*, vol. 39, no. 3, pp. 609–618, 1994.

[33] S. Nakajima, H. Atsumi, R. Kikinis, T. M. Moriarty, D. C. Metcalf, F. A. Jolesz, and P. M. Black, "Use of cortical surface vessel registration for image-guided neurosurgery," *Neurosurgery*, vol. 40, no. 6, pp. 1201–1208, 1997.

[34] C. Studholme, D. L. G. Hill, and D. J. Hawkes, "An overlap invariant entropy measure of 3d medical image alignment," *Pattern Recognit.*, vol. 32, no. 1, pp. 71–86, 1999.

[35] W. H. Press, S. A. Teukolsky, W. T. Vetterling, and B. P. Flannery, *Numerical Recipes in C: The Art of Scientific Computing*, 2nd ed. New York, N.Y.: Cambridge Univ. Press, 1992.

[36] V. R. Mandava, "Three-dimensional multimodal image registration using implanted markers," Ph.D. dissertation, Vanderbilt Univ., Nashville, Tenn., December 1991.

[37] V. R. Mandava et al., "Registration of multimodal volume head images via attached markers," in *Proc. SPIE Medical Imaging IV: Image Processing*, vol. 1652, 1992, pp. 271–282.

[38] B. Rosner, *Fundamentals of Biostatistics*, 4th ed. Belmont, Calif.: Duxbury, 1995.

[39] F. Glover, "Tabu search: A tutorial," *Interfaces*, vol. 20, no. 4, pp. 74–94, 1990.

[40] A. Hertz, E. Taillard, and D. de Werra, *Local Search in Combinatorial Optimization*. New York: Wiley, 1997.

[41] D. J. Hawkes, C. Studholme, and D. L. Hill, "Accuracy, precision, and robustness of fully automated 3D neuro-image registration by multi-resolution optimization of mutual information (MOMI)," *Radiology*, vol. 205, pp. 111–111, 1997.

[42] O. Skrinjar, D. Spencer, and J. Duncan, "Brain shift modeling for use in neurosurgery," in *Medical Image Computing and Computer-Assisted Intervention—Miccai'98*, vol. 1496, LECTURE NOTES IN COMPUTER SCIENCE, pp. 641–649, 1998.

[43] M. I. Miga, K. D. Paulsen, J. M. Lemery, S. D. Eisner, A. Hartov, F. E. Kennedy, and D. W. Roberts, "Model-updated image guidance: Initial clinical experiences with gravity-induced brain deformation," *IEEE Transactions on Medical Imaging*, vol. 18, pp. 866–874, 1999.

[44] C. Davatzikos, D. G. Shen, A. Mohamed, and S. K. Kyriacou, "A framework for predictive modeling of anatomical deformations," *IEEE Transactions on Medical Imaging*, vol. 20, pp. 836–843, 2001.

[45] M. I. Miga, T. K. Sinha, D. M. Cash, R. L. Galloway Jr., and R. J. Weil, "Cortical surface registration for image-guided neurosurgery using laser-range scanning," *IEEE Transactions on Medical Imaging*, vol. (in press), 2003.

[46] M. A. Biot, "General theory of three-dimensional consolidation," *Journal of Applied Physics*, vol. 12, pp. 155–164, 1941.

[47] T. Nagashima, S. Takayuki, and S. I. Rapoport, "A two-dimensional, finite element analysis of vasogenic brain edema," *Neurol Med Chir (Tokyo)*, vol. 20, pp. 1–9, 1990.

[48] K. D. Paulsen, M. I. Miga, F. E. Kennedy, P. J. Hoopes, A. Hartov, and D. W. Roberts, "A computational model for tracking subsurface tissue deformation during stereotactic neurosurgery," *IEEE Transactions on Biomedical Engineering*, vol. 46, pp. 213–225, 1999.

[49] M. Ferrant, A. Nabavi, B. Macq, P. M. Black, F. A. Jolesz, R. Kikinis, and S. K. Warfield, "Serial registration of intra-operative MR images of the brain," *Medical Image Analysis*, vol. 6, pp. 337–359, 2002,

[50] P. J. Basser, "Interstitial pressure, volume, and flow during infusion into brain tissue," *Microvasc. Res.*, vol. 44, pp. 143–165, 1992.

What is claimed is:

1. A method of compensation for intra-operative brain shift of a living subject, comprising the steps of:

a. pro-operatively acquiring brain images of the living subject;

b. constructing a statistical atlas, [E], of brain displacements of the living subject from the pro-operatively acquired brain images, wherein [E] comprises a distribution of brain shift solutions corresponding to a pre-operative surgical plan and is in the form of an n×m matrix with n, m being integers;

c. intra-operatively measuring brain displacements, $\{f\}$, of the living subject, wherein $\{f\}$ is in the form of a n×1 matrix;

d. deriving an intra-operative displacement atlas, $[X_f]$, from the intra-operatively measured brain displacements $\{f\}$ and the statistical atlas [E];

e. obtaining intra-operative brain shift at least from the intra-operative displacement atlas $[X_f]$; and f. compensating for the intra-operative brain shift.

2. The method of claim 1, wherein the pro-operatively acquired brain images of the living subject comprise image data with respect to the brain surface geometry.

3. The method of claim 2, wherein the image data with respect to the brain surface geometry is obtained through the use of at least one of positron emission tomography device, electroencephalography device, computer tomography device, functional magnetic resonance imaging device, magnetic resonance imaging device, and ultrasound imaging device.

4. The method of claim 1, wherein the step of constructing the statistical atlas [E] of brain displacements of the living subject comprises the steps of:
  a. obtaining m model solutions corresponding to the pre-operative surgical plan for the living subject using a finite element mesh having n nodes, and
  b. generating the statistical atlas [E] in the form of an n×m matrix with each model solution, E, which is in the form of a n×1 matrix, forming a column of the matrix.

5. The method of claim 4, wherein the pre-operative surgical plan provides a range of orientations of the head of the living subject with respect to the direction of gravity and amounts of cerebrospinal fluid drainage of the brain of the living subject.

6. The method of claim 5, wherein the model solutions are obtained by solving the equations of:

$$\nabla \cdot G \nabla U + \nabla \frac{G}{1-2v}(\nabla \cdot U) - \alpha \nabla p + (\rho_t - \rho_f)g = 0; \text{ and} \quad \text{(i).}$$

$$\alpha \frac{\partial}{\partial t}(\nabla \cdot U) + \frac{1}{S}\frac{\partial p}{\partial t} - \nabla \cdot k \nabla p = 0, \quad \text{(ii).}$$

wherein U is a displacement vector, G is a shear modulus, $v$ is a Poisson's ratio, p is an interstitial fluid pressure, $\alpha$ is a ratio of fluid volume extracted to volume change of the tissue under compression, k is a hydraulic conductivity, 1/S is an amount of fluid forced into the tissue under constant volume, $\rho_t$ is the density of tissue, $\rho_f$ is the density of fluid, and g is the gravitational acceleration vector.

7. The method of claim 6, wherein the statistical atlas [E] is in the form of $$[E] = \{E_{ij}\} = \begin{bmatrix} U_1^1 & U_1^2 & \cdots & \cdots & U_1^m \\ U_2^1 & U_2^2 & \cdots & \cdots & U_2^m \\ \cdots & \cdots & \cdots & \cdots & \cdots \\ \cdots & \cdots & \cdots & \cdots & \cdots \\ U_n^1 & U_n^2 & \cdots & \cdots & U_n^m \end{bmatrix},$$

wherein $E_{ij}=U_i^j$ is a brain displacement value for i-th nodal position on the finite element mesh at the j-th orientation and cerebrospinal fluid drainage level, and wherein $1 \leq i \leq n$, and $1 \leq j \leq m$.

8. The method of claim 7, wherein the step of obtaining the intra-operative brain shift comprises the steps of:
  a. minimizing the function $\|[E]\{x\}-\{f\}\|$ subject to $\{x\} \geq 0$, so as to obtain regression coefficients $\{x\}$, wherein the sum of the regression coefficients $\{x\}$ is subject to unity; and
  b. calculating the intra-operative brain shift of the living subject from the following relation:

{Intra-operative brain shift}=$[X_j]*\{x\}$, wherein $\{x\}$ are the regression coefficients obtained in step (a).

9. The method of claim 8, wherein the minimizing step is performed with a least-squares regression algorithm.

10. The method of claim 6, wherein the equations (i) and (ii) are solved further with boundary conditions corresponding to specific structures of the brain of the living subject.

11. The method of claim 10, wherein the specific structures of the brain of the living subject comprise at least one of a falx cerebri, tentorium cerebelli, lateral ventricle, white matter, gray matter, tumor, and any combination thereof.

12. The method of claim 11, wherein the specific structures of the brain of the living subject comprise at least one of edema-induced swelling, mannitoi-induced shrinking, and any combination thereof.

13. The method of claim 1, wherein the step of measuring intra-operative brain displacements is performed with an optical device that is capable of obtaining frequency, intensity and geometric data with respect to the cortical surface of the living subject simultaneously.

14. The method of claim 13, wherein the optical device is a laser range scanner.

15. The method of claim 1, wherein the compensating step comprises the step of updating the pre-operatively acquired images of the living subject with the intra-operatively measured brain displacements.

16. A system of compensation for intra-operative brain shift of a living subject, comprising:
  a. an imaging acquiring device for pro-operatively acquiring brain images of the living subject;
  b. a scanning device for intra-operatively measuring brain displacements of the living subject; and
  c. at least one computer coupled with the image acquiring device and the scanning device and adapted for performing the steps of:
    i). constructing a statistical atlas of brain displacements of the living subject from the pro-operatively acquired brain images, wherein the statistical atlas comprises a distribution of brain shift solutions corresponding to a pre-operative surgical plan;
    ii). deriving an intra-operative displacement atlas from the intra-operatively measured brain displacements and the statistical atlas;
    iii). obtaining intra-operative brain shift at least from the intra-operative displacement atlas; and
    iv). compensating for the intra-operative brain shift.

17. The system of claim 16, further comprising a display device coupled to the at least one computer for displaying the brain shift dynamically to facilitate the diagnostic or surgical procedure.

18. The system of claim 16, wherein the imaging acquiring device comprises at least one of positron emission tomography device, electroencephalography device, computer tomography device, functional magnetic resonance imaging device, magnetic resonance imaging device, and ultrasound imaging device.

19. The system of claim 16, wherein the scanning device comprises a laser range scanner that is capable of obtaining frequency, intensity and geometric data with respect to the cortical surface of the living subject simultaneously.

20. The system of claim 16, wherein the scanning device comprises an ultrasound imaging device.

21. The system of claim 16, wherein the step of constructing the statistical atlas of brain displacements of the living subject comprises the steps of:

a. obtaining m model solutions corresponding to the pre-operative surgical plan for the living subject using a finite element mesh having n nodes, wherein m, n being integers; and b. generating the statistical atlas in the form of an n×m matrix, [E], with each model solution, E, which is in the form of a n×1 matrix, forming a column of the matrix.

22. The system of claim 21, wherein the pre-operative surgical plan provides a range of orientations of the head of the living subject with respect to the direction of gravity and amounts of cerebrospinal fluid drainage of the brain of the living subject.

23. The system of claim 22, wherein the model solutions are obtained by solving the equations of:

$$\nabla \cdot G \nabla U + \nabla \frac{G}{1-2\nu}(\nabla \cdot U) - \alpha \nabla p + (\rho_t - \rho_f)g = 0; \text{ and} \quad \text{(i).}$$

$$\alpha \frac{\partial}{\partial t}(\nabla \cdot U) + \frac{1}{S}\frac{\partial p}{\partial t} - \nabla \cdot k \nabla p = 0, \quad \text{(ii).}$$

wherein U is a displacement vector, G is a shear modulus, $\nu$ is a Poisson's ratio, p is an interstitial fluid pressure, $\alpha$ is a ratio of fluid volume extracted to volume change of the tissue under compression, k is a hydraulic conductivity, 1/S is an amount of fluid forced into the tissue under constant volume, $\rho_t$ is the density of tissue, $\rho_f$ is the density of fluid, and g is the gravitational acceleration vector.

24. The system of claim 23, wherein the statistical atlas [E] is in the form of $$[E] = \{E_{ij}\} = \begin{bmatrix} U_1^1 & U_1^2 & \cdots & \cdots & U_1^m \\ U_2^1 & U_2^2 & \cdots & \cdots & U_2^m \\ \cdots & \cdots & \cdots & \cdots & \cdots \\ \cdots & \cdots & \cdots & \cdots & \cdots \\ U_n^1 & U_n^2 & \cdots & \cdots & U_n^m \end{bmatrix},$$

wherein $E_{ij} = U_i^j$ is a brain displacement value for i-th nodal position on the finite element mesh at the j-th orientation and cerebrospinal fluid drainage level, and wherein $1 \leq i \leq n$, and $1 \leq j \leq m$.

25. The system of claim 24, wherein the step of obtaining the intra-operative brain shift comprises the steps of:

a. minimizing the function $\|[E]\{x\} - \{f\}\|$ subject to $\{x\} \geq 0$, so as to obtain regression coefficients $\{x\}$, wherein the sum of the regression coefficients $\{x\}$ is subject to unity; and b. calculating the intra-operative brain shift of the living subject from the following relation:

$$\{\text{Intra-operative brain shift}\} = [X_{ij}] * \{x\},$$

wherein $\{x\}$ are the regression coefficients obtained in step (a).

26. The system of claim 25, wherein the minimizing step is performed with a least-squares regression algorithm.

27. The system of claim 23, wherein the equations (i) and (ii) are solved further with boundary conditions corresponding to specific structures of the brain of the living subject.

28. The system of claim 27, wherein the specific structures of the brain of the living subject comprise at least one of a falx cerebri, tentorium cerebelli, lateral ventricle, white matter, gray matter, tumor, and any combination thereof.

29. The system of claim 27, wherein the specific structures of the brain of the living subject comprise at least one of edema-induced swelling, mannitoi-induced shrinking, and any combination thereof.

30. The system of claim 16, wherein the compensating step comprises the step of updating the pre-operatively acquired images of the living subject with the intra-operatively measured brain displacements.

31. A method of compensation for intra-operative brain shift of a living subject, comprising the steps of:

a. constructing a statistical atlas from pre-operatively acquired brain images of the living subject, wherein the statistical atlas comprises a distribution of brain shift solutions corresponding to a pre-operative surgical plan;

b. calculating brain displacements of the living subject from the statistical atlas for a given set of the living subject's orientation and amount of cerebrospinal fluid drainage;

c. intra-operatively measuring brain displacements of the living subject;

d. obtaining the intra-operative brain shift from the calculated brain displacements and the measured brain displacements; and e. compensating for the intra-operative brain shift.

32. The method of claim 31, wherein the intra-operative brain shift may be corresponding to distributed loading conditions that are associated with gravity, edema-induced swelling, and mannitoi-induced shrinking.

33. The method of claim 31, wherein the intra-operative brain shift may be corresponding to surface-based loading conditions that are associated with tissue retraction, tissue resection.

* * * * *